United States Patent [19]

Muller

[11] Patent Number: 4,569,090
[45] Date of Patent: Feb. 11, 1986

[54] DISPOSABLE URINE SPECIMEN COLLECTING DEVICE

[75] Inventor: Louis F. Muller, El Segundo, Calif.

[73] Assignee: Davstar Industries, Inc., Newport Beach, Calif.

[21] Appl. No.: 614,552

[22] Filed: May 29, 1984

[51] Int. Cl.⁴ ............................................. A47K 11/12
[52] U.S. Cl. .................................. 4/144.2; 128/761; 128/762
[58] Field of Search .......................... 4/144.1–144.4; 128/760–762; 604/329, 347, 350

[56] References Cited

U.S. PATENT DOCUMENTS

| | | | |
|---|---|---|---|
| 3,161,891 | 12/1964 | Bauman | 4/144.1 |
| 3,680,543 | 8/1972 | Cox | 4/144.1 X |
| 3,832,738 | 9/1974 | Kliemann | 4/144.1 X |
| 3,943,770 | 3/1976 | McDonald | 4/144.1 X |
| 4,040,791 | 8/1977 | Kuntz | |
| 4,252,132 | 2/1981 | Kuntz | |
| 4,276,889 | 7/1981 | Kuntz et al. | |
| 4,331,162 | 5/1982 | Kuntz et al. | |

FOREIGN PATENT DOCUMENTS

| | | | |
|---|---|---|---|
| 620064 | 5/1961 | Canada | 604/350 |
| 152722 | 2/1932 | Switzerland | 4/144.1 |

Primary Examiner—Charles E. Phillips
Attorney, Agent, or Firm—Henry M. Bissell

[57] ABSTRACT

An improved device adapted for selectively, inexpensively, sterilely, and rapidly collecting, in a simple manner, the mid-stream portion of urine during voiding. The components of the device are easy and economical to mass manufacture and assemble and are disposable. They comprise an open topped cup which is preferably generally inverted frusto-conical in shape and has a first small opening in the bottom thereof to drain off the initial portion of urine as it is voided. The cup sidewall has a second opening through which extends the neck of a urine collecting bottle, the open head of which is in the cup interior. A resilient plug, preferably of plastic, releasably grips the neck and seals the bottle to the cup, while shielding the bottle head from direct access of urine as it passes into the cup. The plug has a urine passageway extending upwardly therethrough into contact with the bottle head. An overflow opening, preferably in the form of an inverted triangle, is disposed in the cup sidewall at about the height of the second cup opening. The device includes a cap for closing the bottle after use and has removable closures over its open top, bottom opening and overflow opening for sterile protection. It is immediately useable as soon as the closures are removed.

40 Claims, 14 Drawing Figures

DISPOSABLE URINE SPECIMEN COLLECTING DEVICE

BACKGROUND OF THE INVENTION

1. Field of the Invention

The present invention generally relates to urine specimen collecting means and more particularly to an improved disposable device for effectively, inexpensively and sterilely collecting the mid-stream portion of urine from a patient.

2. Description of the Prior Art

Urine analysis is such a simple, common and useful diagnostic aid that the taking of a urine specimen is generally included in even the simplest of physical examinations. It is important not only as an indicator or detector of certain physical conditions and diseases, but it is also particularly useful in connection with the treatment of infections related to the urinary tract, which are much more common in females than males. However, the problem of collecting a suitable specimen is considerably more complex when a female patient is involved.

Thus, in the collecting of a urine specimen from a female patient, it is important to take the specimen as a "mid-stream" sample. When a female patient voids in the normal manner, the initial portion is more likely to contain contamination from foreign matter than that portion which follows. This is because the initial portion is expelled with less force and usually is voided as a mere trickle which is likely to trail along the labia and pick up whatever contamination is present in those areas. The mid-stream portion is expelled with the greatest force and is most likely to leave the urethral meatus directly as a stream without contacting the labia or, if it does, the labia will have had most of the contamination washed off by the initial portion.

Some practitioners go to considerable lengths in an effort to obtain an uncontaminated urine sample from a female patient. With the patient in a reclining position, an attendant cleanses the area adjacent the urethral meatus with a suitable solution in an effort to wash off the contamination which is generally present in that area. Even with such precautions, however, contamination may develop in the collected urine sample to a level sufficient to give a false or misleading indication of the bacteria level in the sample. Moreover, taking a sample under such conditions is an extremely awkward and uncomfortable experience for the patient and is fairly costly, since the patient is required to be present in the physician's office or a hospital with a special attendant, usually a nurse, administering the procedure.

One conventional device for self administration employs a jar with screw collar and handle, plastic cover and screw cap and three cleansing towels. The cap must first be removed, then the towels are used to cleanse the urethral meatus, etc., after which the user voids an initial portion of urine into a toilet and then catches the mid-stream portion in the jar. The whole procedure is complicated and time-consuming with relatively poor results due to the contamination of a significant proportion of samples taken by this procedure.

What is needed is some simple but effective, foolproof device, preferably disposable after a single use, which a patient can use with a minimum of instructions and without assistance, while voiding in the normal manner. The device should have the capability of receiving the entire amount of voided urine, rejecting the initial portion, selecting a portion corresponding to the mid-stream sample and transferring it to a specimen container, and rejecting the remainder of the voided urine by directing it, together with any overflow from the specimen container, into the toilet on which the patient is positioned in the normal attitude.

Although the device set forth in U.S. Pat. No. 4,040,791 for Specimen Collecting Device accomplishes the foregoing objects, such device has been found to be somewhat complicated and expensive to manufacture. For example, it cannot be made in a single high-speed molding operation but must be assembled from a plurality of parts. Morever, it requires certain close tolerances which demand high quality control. Therefore it is not as simple and inexpensive as one would desire for a disposable device intended for extensive usage. Moreover, it is somewhat difficult to handle and orient while using. Therefore, it would be desirable to provide an improved device of the same general type which would be as efficient but less expensive, and easier to handle, orient and use.

The urine collection devices described and claimed in U.S. Pat. Nos. 4,252,132, 4,276,889 and 4,331,162 offer certain advantages over the device of U.S. Pat. No. 4,040,791, but are nevertheless still relatively expensive, so that they are not ideally suitable for use in large scale examinations in free clinics and the like, where cost is of prime importance. Certain of such devices are also relatively bulky, taking up considerable storage space. Accordingly, the need still exists for a very simple, easy to use, very low cost, small, disposable urine collector suitable for use by both males and females.

SUMMARY OF THE INVENTION

The improved urine collector device of the present invention satisfies all the foregoing needs. The device is substantially as set forth in the Abstract of the Disclosure. Not only is the device easy, simple, rapid and inexpensive to mass produce by a rubber or plastic molding technique or the like, but it can be used without first requiring the user to wash or scrub the urethral meatus, labia, or penis, etc. Moreover, it is highly efficient in isolating and collecting contaminant-free urine from both males and females.

Thus, for example, a female can sit on a toilet and begin voiding into the open top of the cup portion of the device which she easily holds in her hand. This is after the protective top, bottom and side closures are removed from the cup to expose the cup's bottom hole, overflow hole and top entry opening. An initial small volume of urine passes down into the cup, out through the bottom hole in the cup and into the toilet. It is only as urination proceeds that the voiding rate increases to a point where urine collects in the cup and passes up the passageway provided in the cup plug which holds the open head of the collector bottle projecting into the cup. Urine flows into the collector bottle while excess urine passes out the triangular cup overflow hole, as well as out the cup bottom hole. Once the collector bottle is full, it is pulled from the cup and capped, and the cup and plug are disposed of.

The cup, plug, bottle and cap can all be mass produced at very low cost from very thin lightweight rubber, plastic, coated paper, etc. Components such as the cups preferably are shaped to facilitate their stacking before assembly of the devices. Preferably the cups are formed of thin plastic by a vacuum thermoform process, which vastly reduces the tooling cost and accelerates the rate of production.

Of prime importance is the fact that the present device assures the obtaining of contamination-free urine without the user being required to do anything at all except remove the protective cap closures and cap, grasp the cup, then void urine into the cup and remove and cap the specimen bottle. No subjective determination of when first and mid-stream portions of urine arrive and end need be made by the user. No complicated instructions need be read, understood and followed. The urine collection proceeds very rapidly and effectively without error and at minimal cost.

The shape and size of the cup can be selected and adjusted to facilitate most effective handling by the user and mass machine production. The cup need not include compartments, webs, etc. to complicate manufacture. The size and shape of the bottle and plug can also be varied for similar purposes. Further features of the invention are set forth in the following detailed description and accompanying drawings.

DESCRIPTION OF THE DRAWINGS

A better understanding of the present invention may be had from a consideration of the following detailed description, taken in conjunction with the accompanying drawings in which.

DESCRIPTION OF THE PREFERRED EMBODIMENTS

Figure 1:
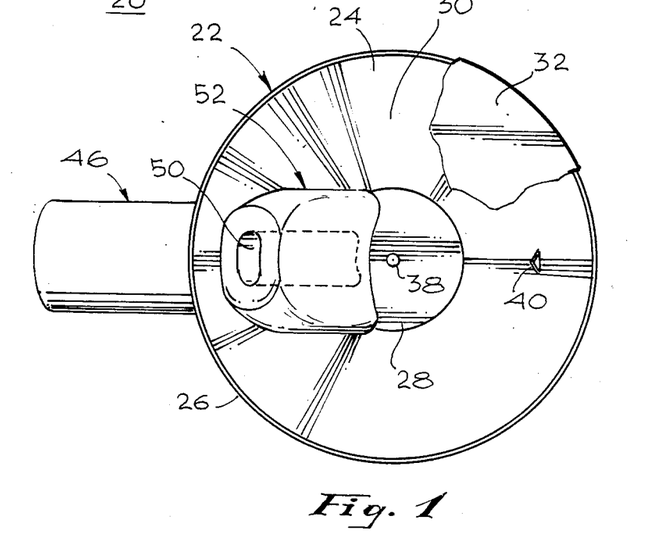
FIG. 1 is a schematic top plan view, partly broken away, of a first preferred embodiment of the improved urine collection device of the present invention.
Figures 2, 3, 5:
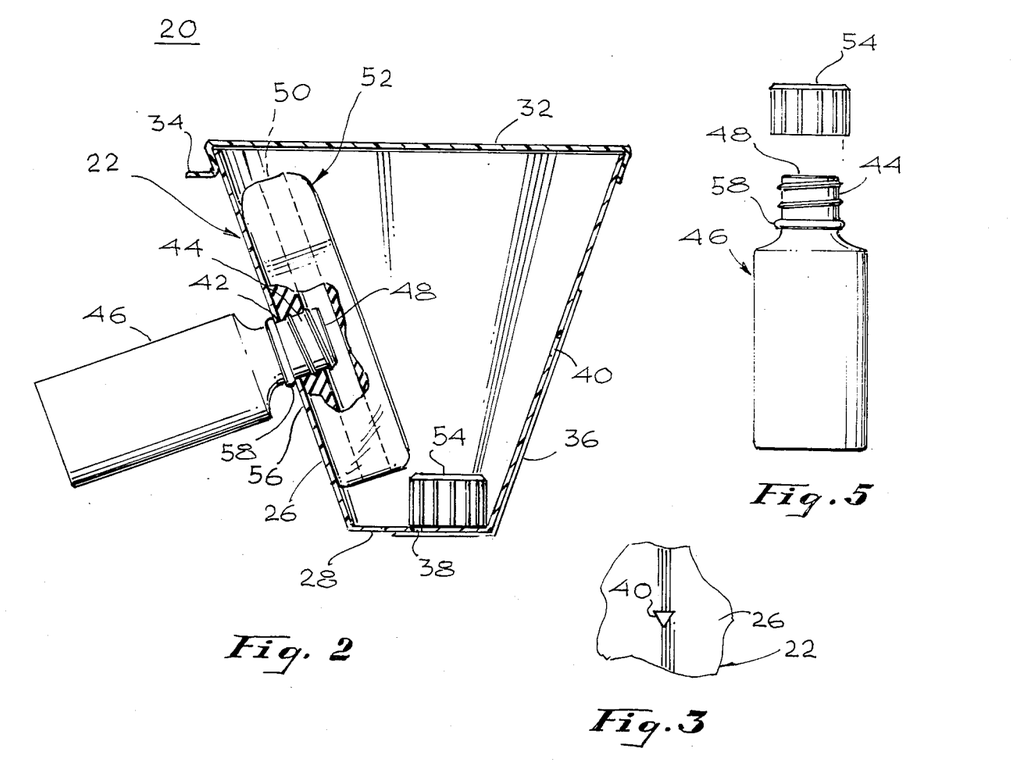
FIG. 2 is a schematic side elevation, partly in section and partly broken away, of the improved device of FIG. 1.
FIG. 3 is a schematic fragmentary front elevation of a portion of the cup of FIG. 1 which contains an inverted triangular overflow opening.
FIG. 5 is a schematic side elevation of the urine collection container of FIG. 1, shown with its screw cap spaced above it.
Figure 4:
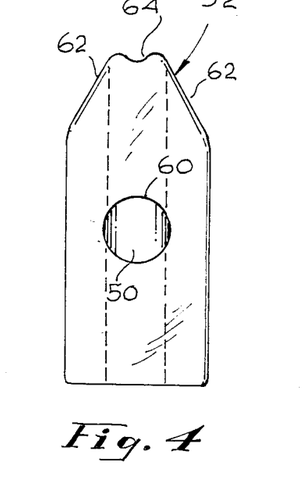
FIG. 4 is a schematic rear elevation of the plug of FIG. 1.

FIGS. 1–5:

Now referring more particularly to FIGS. 1 and 2 of the accompanying drawings, a first preferred embodiment of the improved urine collection device of the present invention is schematically depicted therein. Thus, sterile device 20 is shown comprising a generally inverted frusto-conical cup 22, for example approximately 3.5–4 inches in diameter and 3.0–3.25 inches in length, having an open top 24, closed sidewall 26 and closed bottom 28 defining a central cavity 30. Cup 22 preferably is small, light in weight and has a removable top closure 32 of plastic or the like with pull tab 34 covering top 24, and a peelable adhesive plastic strip 36 or the like removably covering a central bottom urine drain hole 38 of, for example, about 0.125 inch in diameter and an overflow hole 40 in the form of an inverted triangle of, for example, approximately 0.25 inch in height and width.

Hole 40 is positioned in sidewall 26 preferably at a suitable height, for example about 1–1.25 inches above bottom 28 and preferably at least as high as an opening 42 through which the neck 44 of a specimen bottle 46 projects into cavity 30. Hole 40 may be of any suitable shape. However, its preferable inverted triangular form has the effect of automatically increasing the outflow of urine therefrom with a rise in the urine level at the height of the overflow opening 40.

Bottle 46 may be, for example, about 2.5 inches long, with a maximum diameter of, for example about 1 inch. Bottle 46 has an open head 48 disposed within a passageway 50 running the length of a plug 52. Plug 52 releasably grips neck 44 and holds it tightly but releasably in sealing engagement against sidewall 26 to prevent loss of urine through sidewall 26. The frictional engagement between the neck 44 and the plug 52 serves both to hold the bottle 46 in proper position relative to the cup 22 and the urine transfer passage 50 and to retain the plug 52 in sealing engagement with the neck 44 and the inner surface of the cup 22 around the opening 42. Bottle 46 may for example, be blow molded polyethylene or other plastic or the like and includes a preferably plastic, removable screw cap 54 (FIG. 5). Cap 54 is not applied to bottle 46 until the urine specimen has been collected and bottle 46 is separated from cup 22. In order to help seal neck 44 tightly against the outer surface 56 of sidewall 26, neck 44 preferably is provided with an integral expanded ring 58 (FIGS. 2 and 5) which abuts outer surface 56 around opening 42 when neck 44 is fully engaged in and gripped by plug 52.

Plug 52 preferably is somewhat flexible and/or resilient, and may comprise rubber or plastic such as styrofoam or the like in order to releasably but sealingly grip neck 44 and to provide a seal around the opening 42. Thus, neck 44 tightly fits into an opening 60 (FIGS. 2 and 4) in plug 52, which opening intersects passageway 50. Plug 52 is suspended by neck 44 somewhat, e.g. 0.25–0.5 inch, above bottom 28. Plug 52 may have a beveled or sloped upper end 62 to facilitate run-off or urine therefrom and the upper end 64 of passageway 50 may be recessed to prevent inadvertent passage of urine down passageway 50.

Device 20 can be made very inexpensively and is easily disposable. It is preferably supplied in the fully assembled sterile form shown in FIG. 2, and with cap 54 either packed loose inside cavity 30 (see FIG. 2) or in a separate sterile package (not shown), e.g. with a simple instruction sheet.

When it is desired to collect a urine sample, the patient removes top closure 32, drops out cap 54 (if inside cup 22) and places it aside, then removes strip 36 from openings 38 and 40 and discards it. Cup 22 is then held in one hand above a toilet while the patient, if female, sits on the toilet or, if male, sits or stands above the toilet, and the patient voids into cup 22 through top 24, the first stream of urine collecting in the bottom of cavity 30 and running out bottom hole 38 into the toilet. However, the urine level rises in cup 22 as mid-stream urine passes into cup 22 and such mid-stream urine passes up passageway 50 in plug 52 and into bottle 46 through head 48. As bottle 46 fills, excess urine runs out hole 40 into the toilet. The larger the volume of excess urine and the higher the urine level in cup 22, the faster the excess urine passes out hole 40 due to its inverted triangular shape.

After voiding is complete, bottle 46 is pulled from cup 22 and cap 54 is screwed on bottle 46 to seal the urine sample. Any urine remaining in cup 22 may be dumped into the toilet and cup 22 is discarded. Accordingly, device 20 is simple, rapid and inexpensive to make and use. Contaminant-free mid-stream urine specimens are easily and rapidly obtained through normal use of device 20 by the patient without any medical aid or complicated instructions or procedure.

Figure 6:
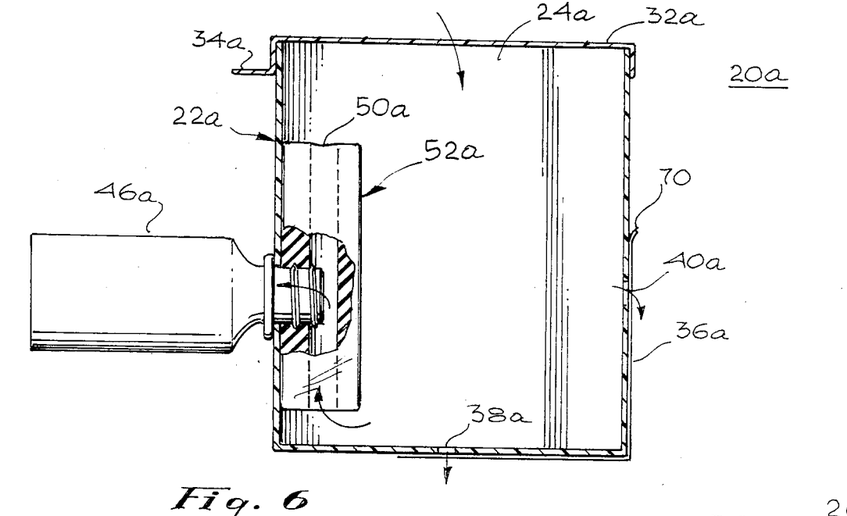
FIG. 6 is a schematic vertical section of a second preferred embodiment of the improved urine collection device of the present invention, shown with its removable cup closures in place.
Figure 7:
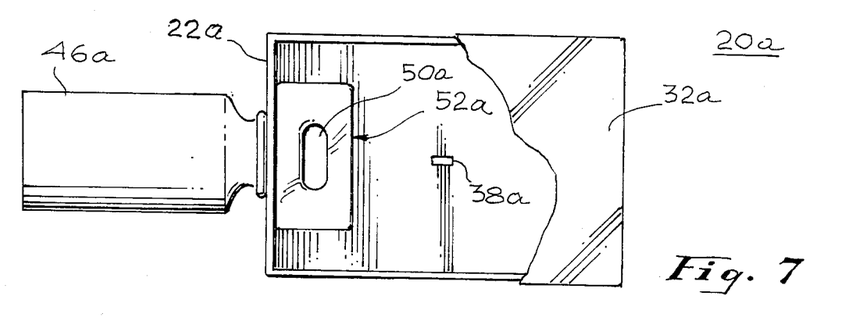
FIG. 7 is a schematic top plan view, partly broken away, of the improved device of FIG. 6.

FIGS. 6–7:

A second preferred embodiment of the improved sterile, disposable urine specimen collecting device of the present invention is schematically depicted in FIGS. 6 and 7. Thus, device 20a is shown. Components thereof similar to those of device 20 bear the same reference numerals but are succeeded by the letter "a". Device 20a differs from device 20 in only a few respects. Thus, device 20a includes cup 22a which is rectangular and of styrofoam plastic. Plug 52a is also rectangular and of resilient rubber, with passageway 50a being vertical. Bottle 46a is disposed horizontally with neck 44a gripped by plug 52a. Openings 38a and 40a are rectangular and are covered by strip 36a having a pull tab 70. Top 24a is covered by cap 32a with tab 34a. Device 20a is simple to pack in the assembled state and has the advantages of device 20.

FIG. 6 may also represent a cylindrical cup and the openings 38a and 40a may be circular if desired. Operation of this device would be similar to that already described.

Figure 8:
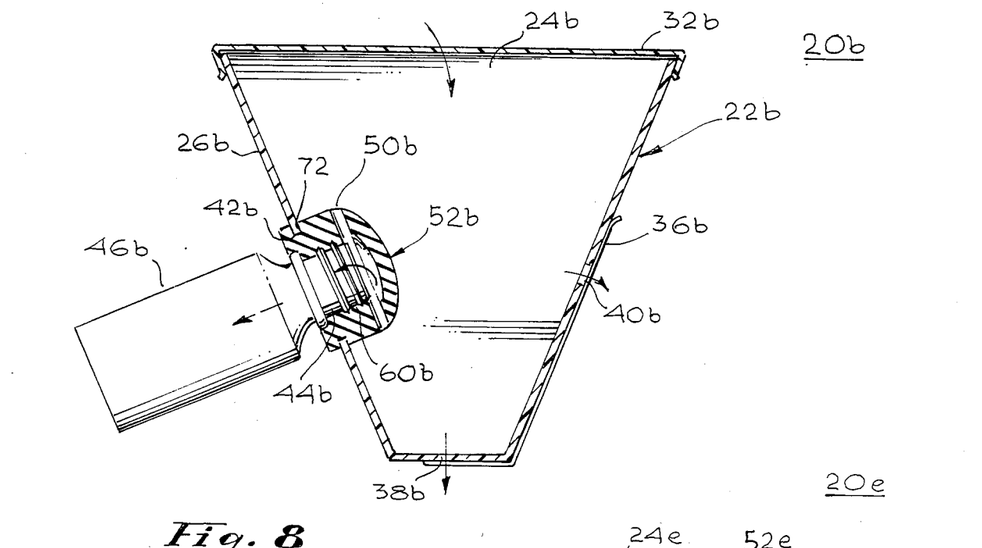
FIG. 8 is a schematic side elevation, partly in section, of a third preferred embodiment of the improved urine collection device of the present invention.
Figure 9:
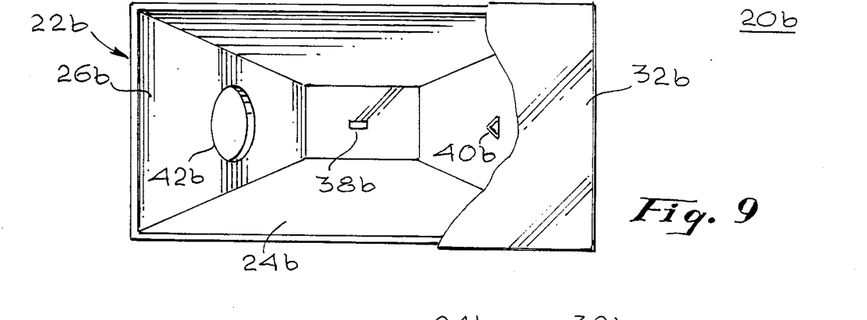
FIG. 9 is a schematic top plan view, partly broken away, of the cup portion of the improved device of FIG. 8.

FIGS. 8–9:

A third preferred embodiment of the improved sterile, disposable, urine specimen collecting device of the present invention is schematically depicted in FIGS. 8 and 9. Thus, device 20b is shown. Components thereof similar to those of device 20 bear the same reference numerals but are succeeded by the letter "b". Device 20b differs from device 20 in only a few respects. Thus, cup 22b is generally inverted frusto-pyramidal in shape rather than being inverted frusto-conical, as with cup 22.

Plug 52b is a resilient rubber or plastic button and has an annular groove 72 in which the portion of sidewall 26b defining opening 42b is sealingly received to hold plug 52b in place in sidewall 26b. Plug 52b includes passageway 50b, and opening 60b in which neck 44b of bottle 46b is sealingly received. Bottom hole 28b is rectangular and hole 40b is inverted triangular, with strip 36b releasably covering these two openings. Snap lid 32b of flexible plastic or the like releasably covers top 24b of cup 22b. A plurality of cups 22b are easy to stack before assembly into device 20b and device 20b also has all the other advantages of device 20.

Figure 10:
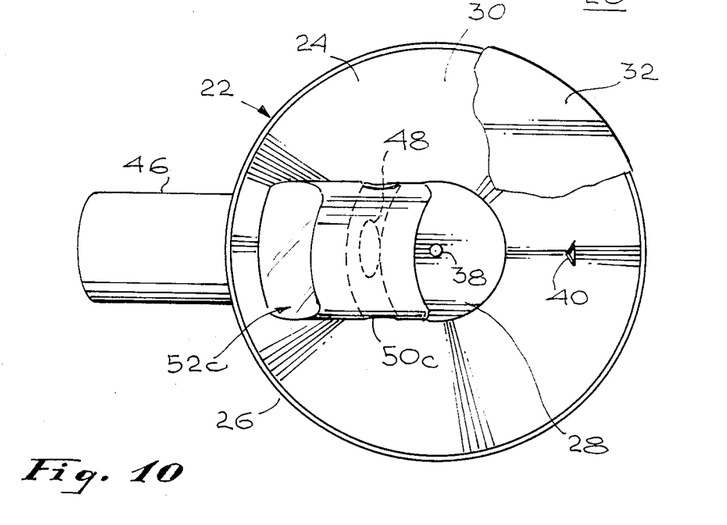
FIG. 10 is a view like FIG. 1, showing an alternative variation of that embodiment.

FIG. 10:

FIG. 10 shows a device exactly like the device 22 shown in FIG. 1 except that the plug 52c is provided with a transverse, generally horizontal passage 50c communicating with the open head 48 of the specimen bottle 46, rather than the generally vertical, longitudinal passage 50 of the plug 52 shown in FIG. 1. The operation of the device 22 of FIG. 10 is essentially the same as the device shown in FIG. 1. The patient voids into the cup 20, and the bottom opening 38 allows the first-voided portion of urine to bleed out of the cup 22. As the cup fills, the mid-stream urine is transferred to the bottle 46 through the passageway 50c. The remaining steps in the process of urine specimen collection are identical to those followed with the cup of FIG. 1.

Figure 11:
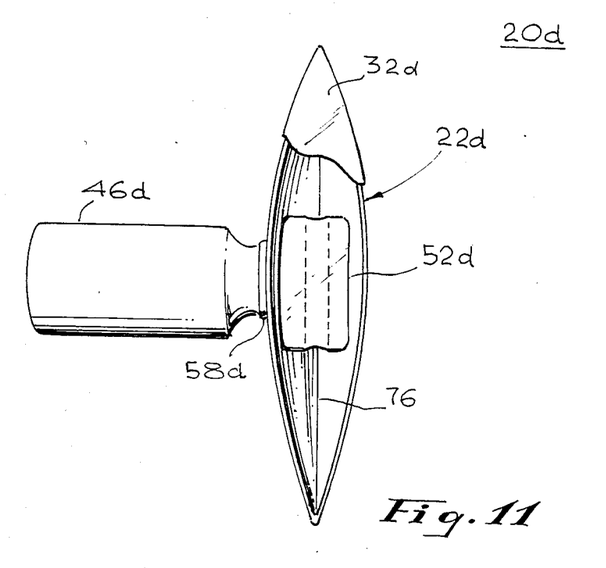
FIG. 11 is a schematic top plan view, partly broken away, of still another embodiment of the present invention.
Figure 12:
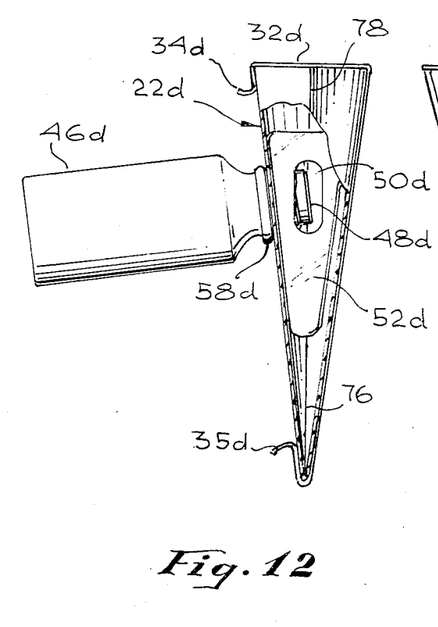
FIG. 12 is a schematic side elevation of the embodiment of FIG. 11.
Figure 13:
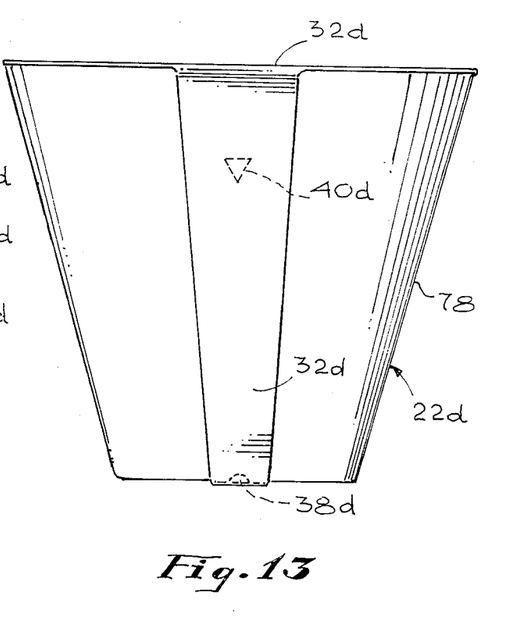
FIG. 13 is a right side elevation of the embodiment of FIGS. 11 and 12.

FIGS. 11–13:

FIGS. 11–13 show still another alternative embodiment of the present invention. Thus device 20d is shown. Components thereof similar to those of device 20 of FIG. 1 bear the same reference numerals but are succeeded by the letter "d". Device 20d differs from device 20 in only a few respects. In this embodiment, the cup 22d is formed with fold lines at opposite edges (inner fold line 76 and outer fold line 78 are shown) which permit the device 22d to be stored and packed in a flatter configuration and with more compact bulk packaging than is possible with any of the other embodiments. Plug 52d serves in the manner already described to retain the specimen bottle 46d in sealing relationship through an opening in the side of the cup 22d and engaged within the plug 52d as previously described. The plug 52d is of resilient plastic or similar material which develops a seal around the opening through which the neck of the bottle 46d is inserted. In this embodiment, the transfer passage 50d is oriented transversely to the plug 52d, in the manner of the plug 52c of the device of FIG. 10.

With the arrangement of FIGS. 11–13, it is possible to seal the cup 22d in sterile fashion by using a single, specially shaped adhesive cover 32d which extends across the opening at the top of the cup 22d, downward along the side opposite the bottle 46d to cover the overflow opening 40d, and under the bottom of the cup 22d to cover the lead opening 38d. For convenience, a second tab 35d is provided at the lower end of the protective seal 32d to facilitate pulling off the seal when the device 20d is to be used.

In use, the patient pulls off the protective covering 32d and grasps the cup 22d in a manner to exert an inward force on the opposed side fold lines 78, thereby squeezing the cup 22d to a generally circular shape so that voiding may be accomplished in the manner described with respect to the embodiment of FIGS. 1–2. The cup 22d may be fabricated of thin plastic or even waterproof paper.

Figure 14:
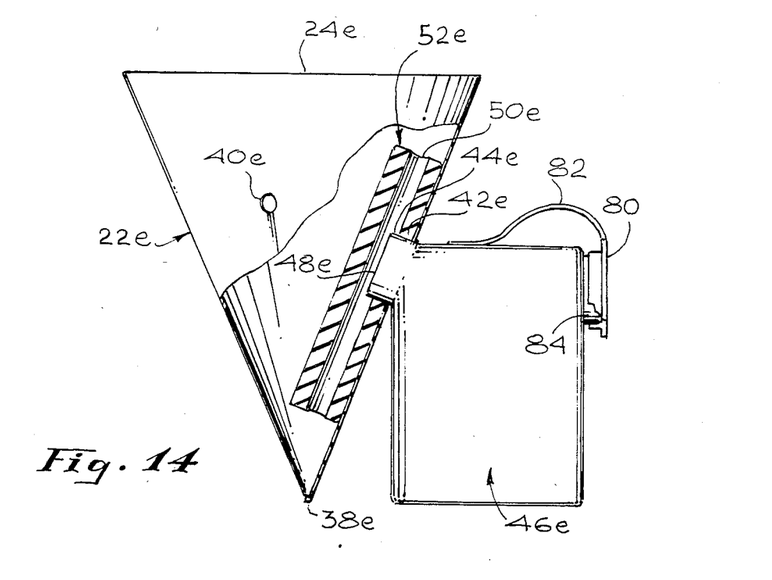
FIG. 14 is a schematic side elevation, partly broken away, of yet another embodiment of the present invention.

FIG. 14:

FIG. 14 shows yet another alternative embodiment of the present invention. Thus device 20e is shown. Components thereof similar to those of device 20 of FIG. 1 bear the same reference numerals but are succeeded by the letter "e". Device 20e differs from device 20 in only a few respects. In this embodiment, the cut 22e is formed as an inverted cone, open at the top and having a small opening 38e as a bleed hole for draining first-voided urine out of the cup and for draining the cup after the mid-stream portion is collected. An overflow opening 40e is provided in the sidewall of the cup 22e, slightly above the passage for transferring the mid-stream portion to the specimen container.

Specimen container 46e is a blow-molded plastic bottle in the general shape of a rectangular parallelepiped, although any other suitable shape developing the desired neck 44e and opening 48e is appropriate. In the configuration shown, the flat bottom of the bottle 46e aligned with the bottom of the cup at 38e forms a stable support base for the collector so that it can be set on a shelf or the like without tipping. The bottle 46e has a cap 80 attached to the bottle 46e by a thin flexible strand 82. The bottle 46e is molded with a post 84 on the rear sidewall for retaining the cap 80 in place. After the device 20e has been used in the manner described, the container 46e is removed from the cup 22e and the cap 80 is removed from the post 84 and placed on the neck 44e, closing and sealing the opening 48e.

The device 20e of FIG. 14 has a plug 52e, shown as a sectional view, with an opening 50e extending through the plug 52e from top to bottom and communicating with the opening 48e of the bottle 46e. As with the previous embodiments, the neck 44e of the bottle 46e is retained in sealing engagement within the opening 42e of the plug 52e and the plug 52e seals the opening in the sidewall of the cup 22e through which the bottle neck 42e extends. When the neck 44e is inserted within the opening 42e of the plug 52e, the expanding configuration of the bottle 46e at the base of the neck 44e bears against the sidewall of the cup 22e to retain the assembly tightly together, thereby insuring the integrity of the plug seal. If need be, a thin adhesive layer may be provided along the surface of the plug 52e which lies against the sidewall of the cup 22e. As manufactured, the device 20e may be sealed in sterile fashion in the manner described hereinabove with respect to the embodiment of FIGS. 1-5, for example, with adhesive sealing strips placed over the top opening 24e, drain opening 38e and overflow opening 40e. These peelable sealing elements are omitted from FIG. 14 for simplicity.

Use of the device of FIG. 14 is generally in the manner previously described. The patient removes the peelable adhesive closures from the openings 24e, 38e and 40e and discards them. The device 20e is then held in one hand and the patient voids into the cup 22e while in the conventional position for urinating into a toilet. Initially voided urine drains slowly through the bleed hole 38e while the cup fills to the level of the bottle opening 48e, rising through the lower portion of the passage 50e and the plug 52e. The upper portion of the plug 52e serves as a deflector. The mid-stream portion of voided urine thereafter transfers into the bottle 46e as the air from the bottle exits through the upper portion of the passage 50e. Should the level of urine rise to the overflow opening 40e, excess urine flows out through that opening and down the side of the cup 22e. After the specimen is collected in the bottle 46e, it is removed from the cup 22e and capped as described above, while the cup 22e with the plug 52e is discarded.

The various arrangements in accordance with the present invention operate in essentially the same manner to collect a mid-stream urine specimen. In order to be effective with the average patient population, the volume of the cup below the level of the opening of the specimen bottle should be approximately 5 cc. With a bottom bleed opening of approximately 0.125 inch diameter, and with an average patient voiding at a rate of approximately 20 cc per second for ten seconds, approximately 13 cc of urine is voided before the sample begins transferring to the specimen bottle. This derives from the approximately 5 cc volume to be filled and approximately 8 cc of urine flowing out the bottom opening before the lower volume of the cup is filled. As the mid-stream portion of voided urine begins to transfer into the specimen bottle, air from the bottle exits through the passageway 50 and the plug 52. It is desirable to have the specimen bottle access at an angle to the horizontal with the opening elevated in order to permit air to escape.

The various arrangements in accordance with the present invention as shown in the accompanying drawings and described hereinabove provide the means whereby an efficient and effective collector for a mid-stream urine specimen can be realized. Furthermore, the design of these embodiments is such that they can be manufactured and distributed at extremely low cost. This economy of production cost results not only from the design of the cup and other elements making up the device so that they may each individually be fabricated at minimum cost without the necessity to resort to relatively costly injection molding processes, but the feature wherein the device with the adhesive covering over the various openings in the cup serves as its own sterile packing also enables the production costs to be kept low with the requirement for a sterile protective package being eliminated. In fact, the cost of forming the cup 22 by vacuum thermoform techniques enables the device to be manufactured for little more than the cost of the bubble pack for comparable urine specimen collectors of the prior art. This is an important and worthwhile consideration for the use of devices of the present invention in economically impoverished areas, such as in underdeveloped countries, where disposable urine specimen collectors such as are presently known and commonly used in this country amount to a luxury which can be ill afforded in such areas.

Although there have been described above specific arrangements of a disposable urine specimen collecting device in accordance with the present invention for the purpose of illustrating the manner in which the invention may be used to advantage, it may be appreciated that the invention is not limited thereto. Accordingly, any and all modifications, variations or equivalent arrangements as may occur to those skilled in the art should be considered to be within the scope of the invention as defined in the annexed claims.

What is claimed is:
1. A urine specimen collector comprising:
   a cup having a top opening for receiving voided urine, a bottom opening of restricted cross section for bleeding the initial portion of voided urine out of the cup at a predetermined rate, and a side opening located a predetermined distance above the bottom opening for receiving the neck of a specimen container therein;
   a specimen container having an extended neck and a neck opening therein for transferring a mid-stream sample of urine into the container while permitting displaced air to flow out of the container, the specimen container being mounted in communication with the cup by insertion of the neck through said side opening; and a plug mounted within the cup in sealing relationship against a sidewall and over said side opening of the cup, said plug defining an opening and a passageway therein, said passageway communicating at one end with a liquid-containing portion of said cup, with said plug opening communicating between said passageway and said neck opening for releasably retaining the neck of the container within the cup while liquid at the level of said neck opening flows into the container from said passageway.

2. The collector of claim 1 wherein the cup is formed with the portion below the side opening being of reduced cross section to limit said portion to a predetermined volume.

3. The collector of claim 2 wherein the sidewalls of the cup are tapered toward each other at the bottom of the cup.

4. The collector of claim 2 wherein said predetermined bleed rate and said predetermined volume are selected to provide that a predetermined amount of initial urine from an average patient is diverted before transfer of the mid-stream sample begins.

5. The collector of claim 4 wherein said predetermined amount of initial urine is approximately 13 cc.

6. The collector of claim 2 wherein the bottom opening is generally circular and is approximately 0.125 inches in diameter, and wherein the portion of the cup below the side opening is approximately 5 cc in volume.

7. The collector of claim 1 further including an overflow opening in a sidewall of the cup, said overflow opening being situated at or above the side opening.

8. The collector of claim 7 wherein the overflow opening is generally triangular in shape and extends upwardly from one angle of the triangle which is located at the level of the top of the side opening.

9. The collector of claim 7 further including removable closures for the bottom, top and overflow openings of the cup to provide an integral self-contained package to maintain sterility of the cup and container after sterilization.

10. The collector of claim 9 wherein said removable closures comprise separate segments of a unitary closure shaped to cover all of said openings.

11. The collector of claim 9 wherein the container is a bottle having a threaded neck and further including a cap for said bottle packed in the cup within said package.

12. The collector of claim 1 wherein the cup is inverted frusto-conical in shape.

13. The collector of claim 1 wherein the cup is in the form of an inverted cone.

14. The collector of claim 1 wherein the cup is formed of two opposite sidewalls joined at bottom and side fold lines, the two sidewalls being deformable by inward forces exerted at the two edge fold lines to establish an opening at the top for receiving voided urine.

15. The collector of claim 1 wherein the cup is formed by vacuum molding.

16. The collector of claim 1 wherein the cup is made of thermoformed plastic.

17. The collector of claim 1 wherein the plug is formed of styrofoam.

18. The collector of claim 1 wherein the plug includes a portion for deflecting urine from entering the bottle directly from the top opening of the cup.

19. The collector of claim 1 wherein the container comprises a bottle having a threaded neck for threadably mounting a cap closure thereon when the bottle is removed from the cup.

20. The collector of claim 1 wherein the container is a blow-molded bottle having a cap removably mounted in storage position on one side of the bottle and attached to the bottle by a thin flexible strand.

21. The collector of claim 20 wherein the bottle has a generally flat bottom situated at the level of the bottom of the cup so as to form a stable base for the collector.

22. The collector of claim 1 wherein the passageway within the plug is generally vertically oriented and extends between an upper end and a lower end of the plug.

23. The collector of claim 22 wherein the side opening is situated approximately midway of the passageway and the portion of the passageway extending above the side opening comprises an air passage for displaced air from the container.

24. The collector of claim 1 wherein the passageway in the plug is generally horizontally oriented, extending transversely from side to side through the plug.

25. The collector of claim 1 wherein the portion of the passageway below the side channel comprises a conduit for conducting mid-stream urine to the neck opening of the container.

26. The collector of claim 25 wherein the conduit is oriented generally vertically to conduct the mid-stream urine from adjacent the bottom of the cup upwardly to the container neck opening.

27. The collector of claim 1 wherein the plug comprises a portion thereof extending through the side opening to provide a seal around the neck of the container and the side opening.

28. A disposable urine specimen collecting device for selectively sterilely collecting the mid-stream portion of urine during voiding, said device comprising:
a urine specimen container including a closed sidewall and bottom defining a urine-receiving space, a main body, and a neck and an open head leading to said space;
a disposable urine collecting cup having a central cavity defined by an open top and closed sidewall and bottom, said cup having a first opening adjacent said bottom for controlled passage of urine therefrom and a second opening in said sidewall above said first opening, said container neck extending through said second opening into said cavity with said container main body outside of said cup; and
a plug releasably securing said container neck in said cavity while sealing said second opening and preventing urine which enters said cavity during voiding from passing directly into said container, said plug including a passageway extending upwardly therethrough from adjacent the bottom thereof and into communication with said second opening and said container head for transferring urine to said container.

29. The improved device of claim 28 wherein said cup is unsegmented and said plug is flexible and resilient.

30. The improved device of claim 28 wherein said cup comprises molded plastic and is generally conical and tapered downwardly to said bottom to facilitate stacking before assembly of said device.

31. The improved device of claim 28 further including overflow means defining a third opening in said sidewall at or above the height of said second opening.

32. The improved device of claim 31 wherein said third opening is triangular with the apex thereof pointing down, so as to automatically accommodate different urine flow rates.

33. The improved device of claim 28 wherein said cup comprises thermoformed plastic, is tapered downwardly and has a plurality of flat sidewalls to facilitate stacking after assembly of said device.

34. The improved device of claim 28 wherein said device includes removable closures over said cup open top, said first opening and said overflow means to maintain said device sterile before use.

35. The improved device of claim 34 wherein said cup removable closures comprise adhesive strips with pull tabs over said first opening and overflow means, and a removable cover with lifting tab.

36. The improved device of claim 28 wherein said plug passageway extends up through the upper end of said plug and exhausts air to facilitate urine flow therein to said open head.

37. The improved device of claim 36 wherein said plug comprises a styrofoam plastic block, the upper end thereof being sloped downwardly to facilitate run-off of urine therefrom.

38. The improved device of claim 37 wherein said cup, container, and cup closures are of lightweight, inexpensive molded plastic.

39. The improved device of claim 36 wherein said plug comprises a flexible, resilient rubber bottom, the lower end of which is spaced above said cup bottom.

40. The improved device of claim 28 wherein said urine specimen container neck includes an integral expanded ring to facilitate sealing of said neck to said cup sidewall by said plug.

* * * * *